United States Patent [19]

Cahalan et al.

[11] Patent Number: 5,415,938
[45] Date of Patent: May 16, 1995

[54] BIOCOMPATABILITY OF SOLID SURFACES

[75] Inventors: Patrick T. Cahalan, Schepersgats; Michel Verhoeven, Maastricht; Marc Hendriks, Brunssum; Linda Cahalan, Schepersgats, all of Netherlands

[73] Assignee: Medtronic, Inc., Minneapolis, Minn.

[21] Appl. No.: 193,964

[22] Filed: Feb. 9, 1994

Related U.S. Application Data

[62] Division of Ser. No. 6,218, Jan. 19, 1993, Pat. No. 5,308,641.

[51] Int. Cl.$^6$ .................................................. A61F 2/01
[52] U.S. Cl. ................................ 428/409; 428/423.5; 428/473.5; 428/525; 435/180; 435/181
[58] Field of Search .................. 428/425.5, 409, 473.5, 428/525; 435/180, 181

[56] References Cited

U.S. PATENT DOCUMENTS

| | | | |
|---|---|---|---|
| 3,826,678 | 7/1974 | Hoffman et al. | |
| 4,273,873 | 6/1981 | Sugitachi et al. | 435/180 |
| 4,378,803 | 4/1983 | Takagi et al. | 604/280 |
| 4,521,564 | 6/1985 | Solomon et al. | |
| 4,560,504 | 12/1985 | Arnold | 260/112 B |
| 4,565,740 | 1/1986 | Golander et al. | |
| 4,720,512 | 1/1988 | Hu et al. | 523/112 |
| 4,921,809 | 5/1990 | Schiff et al. | 436/531 |
| 5,053,048 | 10/1991 | Pinchuk | |
| 5,055,316 | 10/1991 | Hoffman et al. | |
| 5,080,924 | 1/1992 | Kamel et al. | 427/2 |
| 5,132,108 | 7/1992 | Narayanan et al. | |
| 5,134,192 | 7/1992 | Feijen et al. | 525/54.1 |
| 5,217,492 | 6/1993 | Guire et al. | 623/11 |
| 5,229,172 | 7/1993 | Cahalan et al. | 427/536 |

FOREIGN PATENT DOCUMENTS

| | | | |
|---|---|---|---|
| 0152699 | 12/1984 | European Pat. Off. | A61L 33/00 |
| 0351314 | 7/1989 | European Pat. Off. | A61L 33/00 |
| 8700060 | 1/1987 | WIPO | A61L 33/00 |
| 9116932 | 11/1991 | WIPO | A61L 33/00 |

OTHER PUBLICATIONS

"Materials for Enhancing Cell Adhesion by Immobilization of Cell-Adhesive Peptide", by Yoshihiro Ito et al., in the Journal of Biomedical Materials Research, vol. 25, 1325–1337 (1991).

"Adhesion of Cultured Human Endothelial Cells and Adsorption of Serum Proteins on Gas Plasma Treated PTFE Films and ePTFE Graft Material in Relation to the Surface Characteristics", by A. Dekker, et al. in Biomaterials, vol. 12, Mar., 1991.

*Primary Examiner*—James J. Seidleck
*Assistant Examiner*—Patrick R. Delaney
*Attorney, Agent, or Firm*—Daniel W. Latham; Harold R. Patton

[57] ABSTRACT

An improved spacer material for improving the biocompatibility of a biomaterial and a method for making it in which a polyalkylimine is covalently attached to an aminated substrate and combined with a crosslinking agent which is at least difunctional in aldehyde groups. The polyalkylimine can be, for example, polyethyleneimine and the crosslinking agent can be, for example, glutaraldehyde. Preferably, the crosslinking agent is applied in dilute solution and at a pH suitable to accomplish light crosslinking of the polyalkyaimine and also provide aldehyde linkages at the interface between the biomolecule and the spacer.

5 Claims, No Drawings

BIOCOMPATABILITY OF SOLID SURFACES

This is a divisional of application Ser. No. 08/006,218, filed on Jan. 19, 1993, now U.S. Pat. No. 5,308,641.

BACKGROUND OF THE INVENTION

This invention relates to the enhancement of the biocompatability of various surfaces by binding biomolecules to the surface.

Medical devices which serve as substitute blood vessels, synthetic and intraocular lenses, electrodes, catheters and the like in and on the body or as extracorporeal devices intended to be connected to the body to assist in surgery or dialysis are well known. However, the use of such biomaterials in medical devices can stimulate adverse body responses, including rapid thrombogenic action. Various plasma proteins play a role in initiating platelet and fibrin deposition on plastic surfaces. These actions lead to vascular constriction to hinder blood flow, and the inflammatory reaction that follows can lead to the loss of function of the medical device.

A "biomaterial" may be defined as a material that is substantially insoluble in body fluids and that is designed and constructed to be placed in or onto the body or to contact fluid of the body. Ideally, a biomaterial will not induce undesirable reactions in the body such as blood clotting, tissue death, tumor formation, allergic reaction, foreign body reaction (rejection) or inflammatory reaction; will have the physical properties such as strength, elasticity, permeability and flexibility required to function for the intended purpose; can be purified, fabricated and sterilized easily; will substantially maintain its physical properties and function during the time that it remains implanted in or in contact with the body.

As used herein, the solid surface of a biomaterial is characterized as "biocompatible" if it is capable of functioning or existing in contact with biological fluid and/or tissue of a living organism with a net beneficial effect on the living organism. Long term biocompatibility is desired for the purpose of reducing disturbance of the host organism. One approach to improved biocompatibility for biomaterials is to attach various "biomolecules" which can promote the attachment and growth of a normal cell layer such that the body accepts the cell-attached device as a normal part of the body. Biomolecules such as growth factors and cell attachment proteins which have been attached to the device surface could be used for this purpose. In addition, biomolecules such as antithrombogenics, antiplatelets, anti-inflammatories and the like have also been used to improve the biocompatibility of surfaces.

A number of approaches have been suggested to attach such biomolecules. One such approach is set forth in Dekker et al., "Adhesion of endothelial cells and adsorption of serum proteins on gas plasma-treated polytetrafluoroethylene", Biomaterials, vol. 12 March 1991. In that approach, PTFE substrates were modified by radiofrequency plasma to improve the wettability of the surface. Human serum albumin, human fibronectin, human immunoglobulin and human high-density lipoprotein were adsorbed to the plasma-treated substrates followed by seeding with human endothelial cells. Another approach is described in U.S. Pat. No. 5,055,316 to Hoffman et al in which a serum protein such as albumin, an immunoglobulin, a fibrinogen, a fibronectin, a Protein-A or a glycoprotein is bound to a surface by first using plasma gas discharge in the presence of a plasma-polymerizable fluorinated hydrocarbon gas to provide a plasma-deposited surface, followed by exposure to a solution of the protein. Also, for example, covalent attachment of such biomolecules can be found in Ito et al., "Materials for Enhancing Cell Adhesion by Immobilization of Cell-Adhesive Peptide", Journal of Biomedical Materials Research, 25:1325–1337 (1991) in which fibronectin or RGD peptide are bonded by the use of a water soluble carbodiimide. However, these methods immobilize the biomolecule closely to the biomaterial surface thus reducing the availability of the biomolecule for interaction with, for example, cells intended to adhere to the biomolecule.

Spacer molecules have been used to address this problem. A spacer molecule is a molecule or compound which is capable of attachment to a solid surface, is large enough to extend from the surface of said surface and is capable of immobilizing a biomolecule and/or biomolecules. The spacer insures that the active site of the biomolecule is held outward away from the support so as to contact the body fluid efficiently. The spacers are derived from organic molecules having at least two reactive functional groups generally situated at opposing ends of the molecule. Such groups serve as attachment vehicles capable of coupling the spacer to the solid surface and to the biomolecule. For example, in U.S. Pat. No. 5,132,108 to Narayanan et al., a copolymer surface was subjected to radiofrequency plasma treatment by subjecting it to a radiofrequency electric field in the presence of a water vapor plasma medium. An aqueous solution of polyethyleneimine (PEI) and 1-(3-dimethylpropyl)-3-carbodiimide (EDC) coupling agent was applied to the radiofrequency plasma discharge modified polyurethane surface. An aqueous solution of heparin and EDC was then applied to the PEI-treated surface in order to provide a polymeric surface having an anti-thrombogenic agent secured to its surface. However, the addition of such spacer molecules to implanted medical device surfaces also adds instability to the surfaces and increases the prospect for burial of the attached biomolecule in the spacer layer and also for damage to the surfaces as the device is handled or implanted.

Additional stability can be provided, for example, according to U.S. Pat. No. 4,565,740 to Golander et al. or U.S. Pat. No. 5,049,403 to Lars et al. In the first of these patents, a complex of a polymeric cationic surfactant (e.g. a polyalkylamine) and a dialdehyde (e.g. glutaraldehyde) is adsorbed onto a substrate material. In the second of these patents, a polyamine is adsorbed onto the surface of a substrate and crosslinked with crotonaldehyde. However, these crosslinked coatings rely on adsorption onto the surface and ionic bonding to the surface, which may not provide good bonding of the coating to the surface. Multiple coatings, including intermediate layers of anionic material, may be needed to provide an effective coating.

It is therefore an object of the invention to provide a surface for the attachment of biomolecules with a spacer of improved stability during handling and implantation of an implantable medical device.

It is also an object of the invention to provide a spacer which presents a stable platform for the attachment of the biomolecule and thereby prevents the attached biomolecule from being buried in the spacer layer.

It is also an object of the invention to provide a spacer which is strongly attached to the material surface.

SUMMARY OF THE INVENTION

We have discovered an improved spacer material and a method for making it comprising, in combination, an aminated substrate, a polyalkylimine covalently attached to the aminated substrate and a crosslinking agent which is at least difunctional in aldehyde groups. The polyalkylimine can be, for example, polyethyleneimine and the crosslinking agent can be, for example, glutaraldehyde. This spacer can be made by applying a polyalkylimine to the solid surface and then treating the applied polyalkylimine with a crosslinking agent which is at least difunctional in aldehyde groups. Preferably, the crosslinking agent used to crosslink the polyalkylimine is applied in dilute solution and at a suitable pH to accomplish light crosslinking of the polyalkylimine and also with sufficient aldehyde linkages at the interface between the biomolecule and the polyalkylimine to provide light crosslinking with the attached biomolecule.

The polyalkylimine is covalently bonded to the solid surface, for example, by activating the solid surface by contacting amine groups on the solid surface with an activating agent which contains at least two aldehyde groups and then contacting the activated surface with the polyalkylimine. If desired, the activating agent used to covalently bond the polyalkylimine can be the same as the crosslinking agent used to crosslink the polyalkylimine. In the event that there is an inadequate density of amine groups on the solid surface to be activated by the aldehyde activating agent, such amine groups can be provided by grafting amine-containing chemical moieties to the surface by methods well known to those skilled in the art.

In another aspect of the invention, a method for covalent coupling of a polyalkylimine to a solid surface is used in which a second spacer molecule having at least one primary or secondary amine group extending away from the surface is attached to the solid surface followed by activation of the second spacer by contacting the amine group on the second spacer molecule with an activating agent which is at least difunctional in aldehyde groups and then contacting the activated spacer with the polyalkylimine. This second spacer molecule can be, for example, a diamine or an amino-alcohol. The spacer molecule could be attached to the solid surface by any method known to those skilled in the art. In a preferred method of attachment, an aminated surface is first activated by contact with an aldehyde activating agent such as glutaraldehyde followed by contacting the activated surface with the diamine spacer to bind the diamine to the surface and provide an amine group extending away from the surface.

In a preferred embodiment, the spacer molecule of the present invention is used to attach a cellular adhesive molecule to a solid surface. A polyalkylimine is first applied to the solid surface and then treated with a crosslinking agent which is at least difunctional in aldehyde groups. The cellular adhesive molecule is then coupled to the treated polyalkylimine. For example, the cellular adhesive molecule can be fibronectin or RGD peptide which are well known to improve cellular adhesion. The effect of the crosslinked polyalkylimine spacer is to prevent the cellular adhesive molecule from becoming buried in the graft and losing bioactivity. Furthermore, the two layers (polyalkylimine and cellular adhesive molecule layers) have a difference in hydrophilicity that prevents the layers from intermixing.

The cellular adhesive coupling is preferably completed by contacting the treated polyalkylimine with a solution of the cellular adhesive and then applying a mild reducing agent like cyanoborohydride to the cellular adhesive. Reducing agent and cellular adhesive can also be added Simultaneously to the treated polyalkylimine. The effect of this mild reducing treatment is to stabilize the labile bonds between the aldehyde groups of the cross-linking agent and the amine groups of the cellular adhesive and the polyalkyl spacer.

DETAILED DESCRIPTION OF THE INVENTION

In the present invention, a polyalkylimine and a crosslinking agent which is at least difunctional in aldehyde groups are covalently attached to an aminated surface and are employed to provide a spacer on a solid surface for the purpose of improving its biocompatibility.

The solid surface that is rendered biocompatible is desirably of a synthetic or natural material that is insoluble in physiological fluids. The surface may be one or more surfaces of devices intended to function in contact with tissue and/or fluids of living organisms. The substrate for this solid surface of the device may be any suitable metal such as polished titanium or stainless steel or a polymer such as polyurethane, polyvinylpyrrolidone, silicone elastomers, polyolefins such as polyethylene or polypropylene, polytetrafluoroethylene, polyvinyl chloride, polyesters, fluoropolymers, polyacrylates (including polymethacrylates); minerals or ceramics such as hydroxyapatite; human or animal tissue such as bone, skin and teeth; organic materials such as wood, cellulose and compressed carbon; and other natural and synthetic materials such as glass, rubber, wood and the like. Examples of devices which may be provided with biocompatible surfaces in accordance with this invention include vascular graft tubing, dialysis tubing or membrane, blood oxygenator tubing or membrane, ultrafiltration membrane, intra aortic balloon, blood bag, catheter, suture, soft or hard tissue prosthesis, synthetic prosthesis, artificial organs, and lenses for the eye such as contact and intraocular lenses.

The polyalkylimine can be, for example, polyethyleneimine or other branched polyamines. By polyalkylimine we therefore mean to include the water soluble, hydrophilic, polyamines evolving from aziridine and azetidine monomers such as 1-unsubstituted imines, 1-substituted basic imines, activated imines (1-acyl substituted imines), isomeric oxazolines/oxazines and the like. The polyalkylimines employed in the present invention are preferably highly branched, thereby possessing primary, secondary, and tertiary amine groups. Thus, ethyleneimine polymerized by classical cationic chain-growth polymerization, either alone or with other monomers suitable for copolymerization with ethyleneimine, could be used in the present invention.

The crosslinking agent employed in the present invention can be any crosslinking agent which is at least difunctional in aldehyde groups. For example, glutaraldehyde, glyoxal, malonaldehyde, succinaldehyde, adipaldehyde, and dialdehyde starch could be used. The spacer of the present invention can therefore be made by applying a polyalkylimine to the solid surface and then treating the applied polyalkylimine with the crosslinking agent. Preferably, the crosslinking agent used to crosslink the polyalkylimine is applied in dilute solution and at a suitable pH to accomplish light crosslinking and to provide aldehyde functionality for the polyalkylimine surface that will allow biomolecules to readily bond to the spacer. For example, an aldehyde solution that has a concentration in the range of about 0.0005M to about 0.05M could be used while a concentration in the range of about 0.0005M to about 0.005M would be preferred. Also, for example, a pH for the aldehyde solution in the range of about 7 to about 10 would be preferred. The time required to complete the light crosslinking reaction is typically just a few minutes.

The polyalkylimine is covalently bonded to the solid surface, for example, by activating the solid surface by contacting amine groups on the solid surface with an activating agent which is at least difunctional in aldehyde groups and then contacting the activated surface with the polyalkylimine. If desired, the activating agent used to covalently bond the polyalkylimine can be the same as the crosslinking agent used to crosslink the polyalkylimine after it has been applied to the solid surface. In that case, the procedure for making the covalent bonds is essentially the same as is required for the crosslinking reaction described above except that the aldehyde concentration and/or reaction time used may be greater in order to ensure the presence of adequate aldehyde functionality on the activated surface. In the event that there is an inadequate density of amine groups on the solid surface to be attached to the aldehyde activating agent, such amine groups can be provided, for example, by grafting acrylamide to the surface followed by chemical modification to introduce amine groups by methods well known to those skilled in the art. Polyvinyl amines or polyalkylimines can also be covalently attached to polyurethane according to the method taught by U.S. Pat. No. 4,521,564 to Solomon et al. the disclosure of which is incorporated herein by reference. Or, for example, an aminosilane can be attached to the surface as set forth in U.S. Pat. No. 5,053,048 to Pinchuk the disclosure of which is also incorporated herein by reference. Or, for example, a grafted acrylamide-containing polymer can be attached by radiation grafting as set forth in U.S. Pat. No. 3,826,678 to Hoffman et al. the disclosure of which is also incorporated herein by reference.

In another embodiment of the invention, a method for covalent coupling of a polyalkylimine to a solid surface is used in which a second spacer molecule having at least one amine group extending away from the surface is attached to the solid surface followed by activation of the spacer by contacting the amine group on the spacer molecule with a crosslinking agent which is at least difunctional in aldehyde groups and then contacting the activated spacer with the polyalkylimine. The spacer should be a substance containing at least two groups capable of reaction, one of which is an amine group. When the two groups are used, a linear chain is formed. When substances containing more than two groups capable of reaction are involved, the chain will branch out. Substances which are especially suitable for this purpose are aromatic or aliphatic saturated or unsaturated diamines, amino-alcohols, or amino-thiols. Obviously the substance chosen for the second spacer should not contain hydrophobic groups. Saturated aliphatics having a short chain length and containing two groups which are capable of reacting are preferred. For example, the diamines ethylenediamine, tetramethylenediamine, or 1,5-diamine-3-azapentane could be used. The spacer molecule could be attached to the solid Surface by any method known to those skilled in the art. In a preferred method of attachment, an aminated surface is first activated by contact with an aldehyde activating agent followed by contacting the activated surface with the diamine spacer to bind the diamine to the surface and provide an amine group extending away from the surface. The aldehyde activating agent and procedure are essentially the same as described above.

The polyalkylimine spacer of the present invention is used to attach a cellular adhesive molecule or other biomolecule to a solid surface. The biomolecule can be essentially any biomolecule which is attached to the solid surfaces of biomaterials to improve biocompatibility of the biomaterial. The biomolecule may be a growth factor such as endothelial cell growth factor, epithelial cell growth factor, osteoblast growth factor, fibroblast growth factor, platelet derived growth factor, neural growth factor, or angiogenic growth factor; an antimicrobial agent such as lysozyme or penicillin; an antithrombogenic agent such as heparin, fractionated heparins (e.g., on an AT-III column), heparin, heparin sulfate, chondroitin sulfate, modified dextran, albumin, streptokinase, tissue plasminogen activator (TPA) or urokinase; cell attachment proteins such as fibronectin or laminin; a thrombogenic agent such as collagen or a hydrophilic polymer such as hyaluronic acid, chitosan or methyl cellulose, and other proteins, carbohydrates and fatty acids. In a preferred embodiment, the biomolecule is a cellular adhesive molecule.

A polyalkylimine is first applied to the solid surface and then treated with a crosslinking agent which is at least difunctional in aldehyde groups. The cellular adhesive molecule is then coupled to the crosslinked polyalkylimine. For example, the cellular adhesive molecule can be fibronectin or RGD peptide which are well known to improve cellular adhesion. The effect of the crosslinked polyalkylimine is to prevent the cellular adhesive molecule from becoming buried in the graft and losing bioactivity. Furthermore, the two layers (polyalkylimine and cellular adhesive molecule layers) have a difference in hydrophilicity that prevents the layers from intermixing. The cellular adhesive coupling is preferably accomplished by contacting the treated polyalkylimine with a solution of the cellular adhesive and then applying a mild reducing agent like Cyanoborohydride to the cellular adhesive. The effect of this mild reducing treatment is to stabilize the labile bonds between the cellular adhesive molecule and the aldehyde groups of the aldehyde-treated polyalkylimine spacer. Endothelial cells can then be seeded to the cellular adhesive-coated surface by methods known to those skilled in the art.

The following examples provide specific embodiments of the invention.

EXAMPLE 1

Polyurethane samples were provided with a grafted acrylamide surface. The samples were corona treated using a Sherman Treaters corona machine type HT3. The treated sheets were placed in a 40 weight % solution of acrylamide, with stirring, to which 1.75 ml. of a ceric ion solution (made by mixing 13.7 grams of ceric ammonium nitrate (CAN) and 15.75 grams of fuming nitric acid with water to an aqueous solution volume of 250 ml.) was added per 100 grams of acrylamide solution. The test samples were then allowed to react with the monomer solution for one hour at room temperature. The test samples were removed from the monomer solution and thoroughly rinsed with deionized water.

The test samples were then incubated in water overnight at 60° C. to remove loosely bound polymer chains. The samples were then immersed in a 0.2M carbonate buffer pH=10.5 at 60° C. for 3 hours to introduce carboxylic acid groups in the grafted gel.

EXAMPLE 2

Partially hydrolyzed acrylamide-grafted polyurethane samples made as set forth in Example 1 were provided with a covalently attached first spacer molecule by carbodiimide attachment. The samples were placed in a buffer solution (0.5M 4-morpholineethanesulfonic acid pH=5.0) which included the spacer (ethylenediamine; 0.5M concentration). A water soluble carbodiimide (1-(3-dimethylaminopropyl)-3-ethylcarbodiimide hydrochloride was added until a concentration of 0.05M was achieved. Test samples were shaken and reacted at room temperature in the solution for 30 minutes. The solution was then decanted and the samples were thoroughly rinsed with deionized water, 0.2M acetate buffer pH=4.6, 1M NaCl and deionized water again.

EXAMPLE 3

Test samples made according to Example 2 were treated to activate the covalently attached ethylenediamine spacers. The test samples were placed in a 0.1M borate buffered solution of a difunctional aldehyde (glutaraldehyde; 0.5 weight % concentration; pH 9.0). The test samples were shaken in the solution and the reaction was allowed to proceed for one hour at room temperature. The solution was then decanted and the samples were thoroughly rinsed with deionized water.

EXAMPLE 4

Test samples activated according to Example 3 received a coating of a polyalkylimine. The test samples were placed in a 0.1M borate buffered solution of a polyalkylimine (polyethyleneimine; 1 weight % concentration; pH 9.0). The test samples were shaken in the solution for 15 minutes at room temperature. The solution was then decanted and the samples were thoroughly rinsed with deionized water.

EXAMPLE 5

Test samples with attached polyalkylimine made according to Example 4 were subjected to a mild crosslinking/activation treatment with a difunctional aldehyde. The test samples were placed in a 0.1M borate buffered solution of a difunctional aldehyde (glutaraldehyde; 0.05 weight % concentration; pH 9.0). The test samples were shaken in the solution and the reaction was allowed to proceed for fifteen minutes at room temperature. The solution was then decanted and the samples were thoroughly rinsed with deionized water.

EXAMPLE 6

Test samples which have a crosslinked/activated polyalkylimine spacer made according to Example 5 were coupled with a cellular adhesive molecule. 0.01 g of lyophilisate (4,556 weight % fibronectin) was dissolved in 1 ml of deionized water. To the lyophilisate solution, 7 ml of phosphate buffered saline (PBS; 9.0019 g NaCl, 1.1833 g $KH_2PO_4$, 4.3195 g $NaH_2PO_4$ in 1000 ml of deionized water: pH 7.27) was added and allowed to mix. 1 ml of this solution was used to wet the surface of the test sample. The surface was then incubated for 45 minutes at room temperature. The samples were thoroughly rinsed with deionized water.

EXAMPLE 7

Test samples which have been coupled with a cellular adhesive molecule according to Example 6 were stabilized by mild reduction. The test samples coated with fibronectin were placed in a 0.2M acetate buffered solution of a mild reducing agent (0.1M sodium cyanoborohydride; pH 4.62). The test samples were shaken in the solution for one hour at room temperature. The test samples were then copiously rinsed in deionized water and stored in a 0.2M phosphate buffer solution of pH=6.8 containing 0.075 weight % $NaN_3$ at room temperature.

It will be appreciated by those skilled in the art that while the invention has been described above in connection with particular embodiments and examples, the invention is not necessarily so limited and that numerous other embodiments, examples, uses, modifications and departures from the embodiments, examples and uses may be made without departing from the inventive concepts.

We claim:

1. A spacer for attaching a biomolecule to a solid surface comprising, in combination:
   (a) an aminated substrate including acrylamide graft polymerized onto the substrate anal spaced pendant amine groups extending from the graft polyacrylamide and covalently attached to the graft polyacrylamide;
   (b) a polyalkylimine covalently attached to the pendant amine groups of the aminated substrate; and
   (c) a crosslinking agent which is at least difunctional in aldehyde groups providing the covalent attachment of the polyalkylimine to the pendant amine groups of the aminated substrate.

2. The spacer according to claim 1 wherein the polyalkylimine is polyethyleneimine.

3. The spacer according to claim 1 wherein the crosslinking agent is selected from the group consisting of glutaraldehyde, glyoxal, malonaldehyde, succinaldehyde, adipaldehyde, and dialdehyde starch.

4. The spacer according to claim 1 wherein the pendant amine groups are provided by amine-functional spacer molecules covalently attached to the grafted acrylamide.

5. The spacer according to claim 1 wherein the polyalkylimine is also crosslinked by a crosslinking agent which is at least difunctional in aldehyde groups.

* * * * *